US 6,551,958 B1

(12) United States Patent
Baier et al.

(10) Patent No.: US 6,551,958 B1
(45) Date of Patent: Apr. 22, 2003

(54) CATALYST FOR DEHYDROGENATING ETHYL BENZENE TO PRODUCE STYRENE

(75) Inventors: Michael Baier, Mannheim (DE); Otto Hofstadt, Altrip (DE); Wolfgang Jürgen Pöpel, Darmstadt (DE); Hermann Petersen, Grünstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/647,082

(22) PCT Filed: Mar. 29, 1999

(86) PCT No.: PCT/EP99/02146

§ 371 (c)(1),
(2), (4) Date: Sep. 26, 2000

(87) PCT Pub. No.: WO99/49966

PCT Pub. Date: Oct. 7, 1999

(30) Foreign Application Priority Data

Mar. 30, 1998 (DE) .......................... 198 14 080

(51) Int. Cl.[7] .................. B01J 23/00; B01J 23/40; B01J 23/42; B01J 23/58; C07C 2/64
(52) U.S. Cl. .................. 502/304; 502/326; 502/328; 502/330; 502/338; 502/340; 502/344; 585/444
(58) Field of Search ................ 502/304, 306, 502/313, 314, 316, 325, 326, 328, 330, 336, 338, 340, 344; 585/444

(56) References Cited

U.S. PATENT DOCUMENTS

| | | | | |
|---|---|---|---|---|
| 3,904,552 A | * | 9/1975 | O'Hara ...................... 252/458 |
| 4,052,338 A | * | 10/1977 | Riesser ....................... 252/470 |
| 4,098,723 A | * | 7/1978 | Riesser ....................... 252/474 |
| 4,143,083 A | | 3/1979 | Riesser | |
| 4,152,300 A | | 5/1979 | Riesser | |
| 4,460,706 A | * | 7/1984 | Imanari et al. ............. 502/304 |
| 4,749,674 A | * | 6/1988 | Dejaifve et al. ............ 502/304 |
| 4,975,407 A | * | 12/1990 | Dejaifve et al. ............ 502/330 |
| 5,258,348 A | * | 11/1993 | Van Buren et al. ......... 502/328 |
| 5,559,066 A | * | 9/1996 | Poepel et al. ................. 502/20 |
| 5,668,075 A | * | 9/1997 | Milam et al. ............... 502/338 |
| 5,824,831 A | * | 10/1998 | Shiraki et al. .............. 585/444 |
| 5,962,757 A | * | 10/1999 | Milam et al. ............... 585/444 |
| 6,028,027 A | * | 2/2000 | Baier et al. ................. 502/300 |
| 6,166,280 A | * | 12/2000 | Rubin et al. ................ 585/445 |

FOREIGN PATENT DOCUMENTS

| | | |
|---|---|---|
| CA | 2181314 | 1/1998 |
| DE | 40 25 930 | 2/1991 |
| EP | 177 832 | 4/1986 |
| EP | 181 999 | 5/1986 |
| EP | 794 004 | 9/1997 |
| EP | 894 528 | 2/1999 |
| WO | 96/18457 | 6/1996 |
| WO | 96/18594 | 6/1996 |

* cited by examiner

Primary Examiner—Stanley S. Silverman
Assistant Examiner—Cam N. Nguyen
(74) Attorney, Agent, or Firm—Keil & Weinkauf

(57) ABSTRACT

A process for the preparation of a catalyst comprising iron oxide, potassium oxide, a magnesium compound and a cerium compound, wherein the catalyst has one or more Fe/K phases $K_2O \cdot Fe_2O_3$ 1:n, where n is a natural number from 1 to 11, and a process for the dehydrogenation of ethylbenzene to styrene.

7 Claims, No Drawings

CATALYST FOR DEHYDROGENATING ETHYL BENZENE TO PRODUCE STYRENE

BACKGROUND OF THE INVENTION

EP-A 0 181 999 describes a dehydrogenation catalyst which, besides $Fe_2O_3$, $K_2O$ and MgO, may additionally contain chromium and/or manganese, a compound of cerium, molybdenum or tungsten and CaO. The catalysts mentioned in the examples are calcined at temperatures in the range from 510 to 540° C. It is pointed out that the activity of the catalysts, in particular of the selective catalysts, is considerably reduced at relatively high calcination temperatures.

A low calcination temperature (540° C.) is also described in EP-A 0 177 832 for magnesium-containing catalysts based on $Fe_2O_3$ and $K_2O$.

DE-A 28 15 812 describes dehydrogenation catalysts which consist of mixtures of iron oxide, potassium oxide, vanadium oxide and, if desired, chromium oxide. The selectivity and/or conversion rate to unsaturated hydrocarbons from saturated compounds is said to be improved by small amounts of oxygen-containing compounds of aluminum, cadmium, copper, magnesium, manganese, nickel, uranium, zinc or a rare earth and mixtures thereof.

DE 38 21 431 describes a $K_2Fe_{22}O_{34}$-containing catalyst which is calcined at 900° C. For the preparation, exclusively iron-oxide and a potassium compound are employed. The calcination product is subsequently washed and filtered, the resultant product being lamellar plates having a diameter of from 0.5 to 5 μm.

It is an object of the invention to provide a catalyst having improved activity and selectivity in the dehydrogenation of ethylbenzene to styrene. The catalyst should in addition have high mechanical and chemical stability and a good shelf life.

We have found that this object is achieved by a catalyst comprising iron oxide, potassium oxide, a magnesium compound and a cerium compound, where the catalyst has one or more Fe/K phases $K_2O.Fe_2O_3$ 1:n, where n is a natural number from 1 to 11, in particular one of the phases $K_2O.Fe_2O_3$ 1:4 ($K_2Fe_8O_{13}$), $K_2O.Fe_2O_3$ 1:5 ($K_2Fe_{10}O_{16}$) and/or $K_2O.Fe_2O_3$ 1:11 ($K_2Fe_{22}O_{34}$).

The special structural properties compared with the known catalysts include large pore diameters at the same time as high mechanical stability, a large internal surface area, a low weight per liter and the significant formation of X-ray detectable Fe/K phases $K_2O.Fe_2O_3$ 1:4 and/or $K_2O.Fe_2O_3$ 1:11. The best magnesium-containing catalysts known to date do not, owing to the low calcination temperature, contain Fe/K phases, with the exception of small amounts of $K_2Fe_2O_4$, but instead contain only $Fe_2O_3$ (hematite) as iron constituent. The Fe/K phases $K_2O.Fe_2O_3$ 1:4 and $K_2O.Fe_2O_3$ 1:11 apparently only form from 750° C.

The Fe/K phases can be determined radiographically. The lattice plane separations and relative intensities of the Fe/K phases $K_2O.Fe_2O_3$ 1:5 ($K_2Fe_{10}O_{16}$) and/or $K_2O.Fe_2O_3$ 1:11 ($K_2Fe_{22}O_{34}$ in Table 3. Owing to the inclusion of magnesium, cerium and possibly further promoter and added metals in the Fe/K phases, the reflections may be slightly shifted compared with the pure Fe/K phases.

DETAILED DESCRIPTION OF THE INVENTION

Preferred catalysts according to the invention have reflections for lattice plane separations in the following ranges:

| | Lattice plane separation d(Å) | +/− |
|---|---|---|
| 1st reflection | 11.7 | 0.5 |
| 2nd reflection | 5.8 | 0.5 |
| 3rd reflection | 2.97 | 0.1 |
| 4th reflection | 2.82 | 0.1 |
| 5th reflection | 2.65 | 0.05 |
| 6th reflection | 2.56 | 0.05 |
| 7th reflection | 2.45 | 0.05 |
| 8th reflection | 2.37 | 0.05 |
| 9th reflection | 2.26 | 0.05 |
| 10th reflection | 2.15 | 0.05 |
| 11th reflection | 1.69 | 0.02 |
| 12th reflection | 1.65 | 0.02 |
| 13th reflection | 1.48 | 0.02 |

Particularly preferred catalysts have a 1st reflection in the range from 11.70 Å to 11.90 Å, in particular from 11.74 Å to 11.87 Å, and second reflection at from 5.85 Å to 5.95 Å, in particular from 5.89 Å to 5.93 Å.

Preferred catalysts comprise 50–90% by weight of iron, calculated as $Fe_2O_3$, from 1 to 40% by weight of potassium, calculated as $K_2O$, from 5 to 20% by weight of cerium, calculated as $Ce_2O_3$, and from 0.1 to 10% by weight of magnesium, calculated as MgO.

In addition to magnesium and cerium, the catalyst may furthermore comprise one or more further conventional promoters for increasing the selectivity, activity or stability in conventional concentrations. Suitable promoters are compounds of elements selected from the group consisting of Be, Ca, Sr, Ba, Sc, Ti, Zr, Hf, V, Ta, Mo, W, Mn, Tc, Re, Ru, Os, Co, Rh, Ir, Ni, Pd, Pt, Cu, Ag, Au, Zn, Cd, Hg, Al, Ga, In, Tl, Ge, Sn, Pb, Bi, Pr, Nd, Pm, Sm, Eu, Gd, Tb, Dy, Ho, Er, Tm, Yb and Lu, which can be used individually or in mixtures. Preferred additional promoters are compounds selected from the group consisting of Ca, V, Cr, Mo, W, Ti, Mn, Co and Al. Particularly preferred additional promoters are Ca, V, Cr, Mo and W. The additional promoters are preferably added in amounts of in each case from 0 to 15% by weight, in particular from 1 to 10% by weight, calculated as the most stable oxides.

Potassium can be replaced in part or full by equivalent amounts of other alkali metals, for example cesium or sodium.

The novel catalyst preferably comprises iron, potassium, cerium and magnesium and, as further elements, tungsten, molybdenum and calcium. Favorable catalysts are furthermore those which contain vanadium.

The addition of vanadium further increases the selectivity of the catalysts. The addition of vanadium (0.1–10% by weight) is therefore very advantageous.

Elements such as Cr, Al, Ti, Co, Li and Zn are generally present in the catalysts according to the invention in secondary amounts, for example from 0 to 2% by weight, in particular from 0 to 1% by weight, in each case as the oxide.

However, the catalysts preferably contain no chromium.

For example, a novel catalyst comprises, in the ready-to-use state:

- 50–90% by weight, in particular 60–80% by weight, of iron, calculated as $Fe_2O_3$;
- 1–40% by weight, in particular 5–15% by weight of potassium, calculated as $K_2O$;
- 5–20% by weight, in particular 6–15% by weight, of cerium, calculated as $Ce_2O_3$;
- 0.1–10% by weight, in particular 1–5% by weight, of magnesium, calculated as MgO;
- 0–10% by weight, in particular 0.1–4% by weight, of calcium, calculated as CaO;
- 0–10% by weight, in particular 0–5% by weight, of tungsten, calculated as $WO_3$;
- 0–10% by weight, in particular 0–5% by weight, of molybdenum, calculated as $MoO_3$;
- 0–10% by weight, in particular 0.1–4% by weight, of vanadium, calculated as $V_2O_5$, with the proviso that at least 0.1% by weight, in particular 1% by weight, of tungsten or molybdenum is present.

The potassium compound used is preferably potassium carbonate, potassium hydroxide or another potassium compound which can be decomposed at elevated temperatures, such as potassium oxalate. It is also possible to use a potassium compound which contains the proposed promoter (i.e. as the corresponding anion or as a double salt).

The vanadium compound used is preferably $V_2O_5$, ammonium vanadate or alkali metal vanadates.

The magnesium compound used is preferably $Mg(OH)_2$, MgO, $MgCO_3$ or magnesium bicarbonate.

The cerium compound used is preferably $Ce_2O_3$, cerium oxalate or cerium carbonate.

The molybdenum compound used is preferably $MoO_3$, $H_2MoO_4$ or ammonium molybdate.

The tungsten compound used is preferably $WO_3$, $H_2WO_4$ or ammonium tungstite.

The aluminum compound used is preferably Al OOH or $Al_2O_3$.

The calcium compound used is-preferably CaO, $CaCO_3$ or $Ca(OH)_2$.

The novel catalyst is prepared predominantly from $\alpha$-$Fe_2O_3$ instead of the FeOOH preferred in EP-A-0195252 and contains an amount of cerium of up to 20%, calculated as $Ce_2O_3$, which is increased over the recommendation given therein of 3–6% by weight of $Ce_2O_3$. The increased amount of cerium used in the novel catalysts results in an improvement in the activity and long-term stability.

Preference is given to catalysts which have been obtained using $\alpha$-$Fe_2O_3$ (hematite) having a particle size of greater than 0.3 $\mu$m and pore diameters of corresponding size. The catalysts preferably have a mean pore diameter of greater than 0.35 $\mu$m, in particular greater than 0.40 $\mu$m. Pure iron oxide hydroxide (FeOOH) is less suitable for the preparation of the catalysts. Studies on corresponding comparative catalysts show that these have neither the desired large pore diameter nor satisfactory mechanical stability.

Instead of pure $\alpha$-$Fe_2O_3$ (hematitie), however, it is possible to employ mixtures of $\alpha$-$Fe_2O_3$ and $\alpha$-FeOOH (goethite) as the iron component, so long as at least 50% by weight of $\alpha$-$Fe_2O_3$ are used in the preparation. Preference is given to mixtures of from 60 to 90% by weight of $\alpha$-$Fe_2O_3$ and from 10 to 40% by weight of $\alpha$-FeOOH. Although the catalyst prepared by the process according to the invention from a mixture of, for example, 70% by weight of $Fe_2O_3$ and 30% by weight of FeOOH has on average somewhat smaller pore radii and somewhat lower mechanical stability, it has, on the other hand, a significantly larger internal surface area than the catalyst prepared only from $Fe_2O_3$. The consequence is a further improvement in the activity.

In principle, the preparation follows the process given in EP A 0 195 252, but the calcination is carried out at significantly higher temperatures. The improvement produced by the novel catalysts over these known catalysts and those described elsewhere is apparently due to the calcination at temperatures above 750° C., preferably at from 760 to 1000° C., in particular at from 800 to 900° C., and the use of a certain iron modification, magnesium and an increased amount of cerium in an otherwise comparable process. The higher calcination temperature together with the higher amount of cerium and the content of magnesium results in novel, unusual properties of the catalysts and at the same time in a significant improvement in the activity and selectivity. It has been found that this catalyst has excellent productivity and long-term stability as well as good mechanical stability at low vapor/EB ratios (up to V/EB=1.0 kg/kg). Owing to the lower energy consumption of the process operated therewith, it therefore also offers economic advantages over the known catalysts. However, even at the higher vapor/EB ratios of 1.1–1.5 kg/kg which are currently usual, the new catalyst achieves better productivity.

The invention also relates to a process for the dehydrogenation of alkylaromatic or aliphatic hydrocarbons to the corresponding alkenes using the novel catalysts.

Particular preference is given to the dehydrogenation of ethylbenzene to styrene. However, the catalysts may advantageously also be employed for the dehydrogenation of 1,1-diphenylethane (DPEA) to 1,1-diphenylethene (DPE). DPE is in demand as a raw material for styrene copolymers of increased heat resistance.

The following details apply to the preparation of the novel catalysts:

Mixing of the Starting Materials and Preparation of a Shapeable Material

Intimate mixing of the starting materials is important. This can be achieved simply by dry mixing or by suspending the starting materials in water and spray-drying the resultant suspension. During all mixing operations, it is advantageous for all constituents, with the exception of the iron oxide, to be in very finely divided form. After addition of water, a shapeable material is obtained from the mixtures by compounding. The shaping to tablets can, by contrast, be carried out using a dry mix of the constituents.

Production of Moldings

Moldings can be produced by extrusion or by tableting the dry spray powder or a mixture in a tablet press. In this case, it may be beneficial to add tableting auxiliaries (for example graphite or various stearates) to the tableting material. Suitable moldings are extrudates having various geometries, preferably solid extrudates having a diameter of, for example, 3–6 mm. Also suitable are, for example, hollow extrudates or rib or star extrudates (i.e. extrudates having external longitudinal ribs or a star-shaped cross section) or ring tablets having a central hole. The shapeability can be modified using auxiliaries such as stearates, Walocel, starch or the like.

Drying

The drying can be carried out continuously or batchwise. Continuous drying can be carried out using belt dryers and batch drying using tray ovens. On an industrial scale, suitable equipment is that which is suitable for industrial-scale drying processes, such as belt dryers or tray ovens. The usual drying temperatures are 80–140° C. Higher drying temperatures may result in undesired cracking of the moldings owing to an excessive drying rate. Lower drying temperatures are possible, but extend the drying time.

Conditioning; Calcination

After the drying, the moldings are firstly heated at 250–350° C. for about 2 hours ("conditioning"), then at 750–1000° C. for 1–2 hours ("calcination"). In the case of production on an industrial scale, the conditioning and calcination can be carried out in a single operation, for example in a rotating tube with various heating zones. The temperature is then increased in steps from, for example, 250° C. to 800–900° C. After exiting from the rotating tube, the moldings are allowed to cool. Fragments and fine dust are separated off by screening and discarded.

PREPARATION EXAMPLES

Comparative Experiments

Composition and Properties (Summarized in the Tables Below)

The novel catalyst from Example 1 was prepared as described below. The catalysts in the other examples were obtained in a similar manner with corresponding modification of the mixing ratios.

900 g of α-$Fe_2O_3$, in the form of needles having a length of 0.4 μm and a length/width ratio of about 5 were added, with stirring, to a suspension which also contained 200 g of $K_2CO_3$, 200 g of water-containing cerium carbonate (composition of the formula $Ce_2(CO_3)_3 \cdot xH_2O$ having a cerium content of 40% by weight), 40 g of $CaCO_3$, 40 g of $WO_3$ and 60 g of basic magnesium carbonate (composition of the formula $4MgCO_3 \cdot Mg(OH)_2 \cdot 4H_2O$, corresponding to 50 g $MgCO_3$) in 2000 ml of water. The suspension was spray-dried. The spray powder was converted into a pasty material over the course of 30 minutes in a compounder with addition of about 120 ml of water. It was not necessary to modify the shapeability by means of auxiliaries. The material was shaped in an extruder to give cylindrical solid extrudates having a diameter of 3 mm, cut into pieces with a length of about 1 cm, dried in a fan-assisted oven for about 3 hours at 100° C., and, in a calcination oven, first conditioned at 300° C. for 2 hours and then calcined at 760° C.

In Example 8 and Comparative Experiments C1 and C2, some or all of the $Fe_2O_3$ was replaced by the corresponding amount of α-FeOOH (needle-shaped iron oxide yellow having a needle length of about 0.6 μm and a length/diameter ratio of about 6). As soon as the iron oxide had been added, further vigorous stirring or compounding (considerable input of force) was avoided, since it can result in comminution of the iron oxide particles and thus impairment of the properties of the catalyst.

TABLE 1

Composition of novel catalysts in parts by weight (amounts of the constituents in [dg] used in the preparation)

| Example | 1 | 2 | 3 | 4 | 5 | 6 | 7 | 8 | 9 |
|---|---|---|---|---|---|---|---|---|---|
| $Fe_2O_3$ | 90 | 90 | 90 | 90 | 90 | 90 | 90 | 63 | 90 |
| FeOOH | — | — | — | — | — | — | — | 30 | — |
| $K_2CO_3$ | 20 | 20 | 20 | 20 | 20 | 20 | 20 | 20 | 16.6 |
| $Ce_2(CO_3)_3 \cdot xH_2O$ | 20 | 20 | 20 | 20 | 10 | 20 | 20 | 20 | 20 |
| $CaCO_3$ | 4 | 4 | 4 | 4 | 4 | 4 | 4 | 4 | 4.6 |
| $WO_3$ | 4 | 4 | 4 | 4 | 4 | — | 4 | 4 | — |
| $MoO_3$ | — | — | — | — | — | 2.5 | — | — | 2.9 |
| $4MgCO_3 \cdot Mg(OH)_2 \cdot 4H_2O$ | 5.0 | 5.0 | 5.0 | 5.0 | 5.0 | 5.0 | 5.0 | 5.0 | 6.1 |
| $V_2O_5$ | — | — | — | — | — | — | 1.5 | — | — |
| $T_{calc}$ [° C.] | 760 | 800 | 850 | 900 | 850 | 850 | 850 | 850 | 875 |

TABLE 2

Composition of Comparative Experiments C1 to C4 (amount data as above)

| Comparison | C1 | C2 | C3 | C4 |
|---|---|---|---|---|
| FeOOH | 100 | 100 | — | — |
| $Fe_2O_3$ | — | — | 90 | 90 |
| $K_2CO_3$ | 20 | 20 | 20 | 20 |
| $Ce_2(CO_3)_3 \cdot xH_2O$ | 10 | 20 | 20 | 20 |
| $CaCO_3$ | 4 | 4 | 4 | 4 |
| $WO_3$ | 4 | 4 | 4 | 4 |
| $4MgCO_3 \cdot Mg(OH)_2 \cdot 4H_2O$ | — | 5.0 | — | 5.0 |

TABLE 2-continued

Composition of Comparative Experiments C1 to C4 (amount data as above)

| Comparison | C1 | C2 | C3 | C4 |
|---|---|---|---|---|
| $V_2O_5$ | — | — | — | — |
| $T_{calc}$ [° C.] | 850 | 850 | 850 | 700 |

TABLE 3

XRD data for the pure Fe/K phases $K_2Fe_{10}O_{16}$ and $K_2Fe_{22}O_{34}$ and the catalysts from Examples 2 to 7

|  | Example 2 | | Example 3 | | Example 4 | | Example 5 | |
|---|---|---|---|---|---|---|---|---|
|  | d (A) | I (rel) | d (A) | I (rel) | d (A) | I (rel) | d (A) | I (rel) |
| 1st reflection | 11.74681 | 46.4 | 11.74126 | 46.7 | 11.79432 | 47.1 | 11.80807 | 53.6 |
| 2nd reflection | 5.90203 | 64.8 | 5.89902 | 62.8 | 5.90529 | 59.6 | 5.91664 | 66.1 |
| 3rd reflection | 2.97251 | 60.5 | 2.97214 | 64.5 | 2.97420 | 69.1 | 2.97872 | 63.2 |
| 4th reflection | 2.82464 | 84.4 | 2.82720 | 88.5 | 2.82748 | 84.5 | 2.82819 | 95.0 |
| 5th reflection | 2.65730 | 91.3 | 2.65889 | 92.9 | 2.66031 | 84.8 | 2.66518 | 91.5 |
| 6th reflection | 2.56214 | 89.0 | 2.56449 | 93.9 | 2.56718 | 87.5 | 2.56957 | 93.4 |
| 7th reflection | 2.45326 | 43.8 | 2.45054 | 47.8 | 2.45586 | 42.7 | 2.45314 | 43.4 |
| 8th reflection | 2.37752 | 62.3 | 2.37919 | 64.0 | 2.37933 | 61.8 | 2.37994 | 65.9 |
| 9th reflection | 2.26616 | 46.1 | 2.26743 | 46.0 | 2.26836 | 41.0 | 2.26851 | 41.0 |
| 10th reflection | 2.15728 | 39.4 | 2.16120 | 38.3 | 2.16302 | 35.3 | 2.16127 | 38.6 |
| 11th reflection | 1.69149 | 76.5 | 1.69087 | 61.9 | 1.69140 | 59.0 | 1.69169 | 60.7 |
| 12th reflection | 1.65273 | 51.9 | 1.65157 | 51.8 | 1.65262 | 49.8 | 1.65484 | 49.2 |
| 13th reflection | 1.48958 | 100.0 | 1.48998 | 100.0 | 1.48968 | 100.0 | 1.49211 | 100.0 |

|  | Example 6 | | Example 7 | | $K_2Fe_{10}O_{16}$ | | $K_2Fe_{22}O_{34}$ | |
|---|---|---|---|---|---|---|---|---|
|  | d (A) | I (rel) | d (A) | I (rel) | d (A) | I (rel) | d (A) | I (rel) |
| 1st reflection | 11.75676 | 52.3 | 11.86811 | 48.6 | 12.01173 | 100 | 11.90698 | 100.0 |
| 2nd reflection | 5.91687 | 69.5 | 5.92583 | 62.0 | 5.99707 | 45 | 5.95349 | 40 |
|  |  |  |  |  | 4.47162 | 10 | 4.70805 | 20 |
|  |  |  |  |  |  |  | 4.30252 | 12 |
| 3rd reflection | 2.97621 | 67.0 | 2.98083 | 66.7 | 2.99197 | 10 | 2.97458 | 60 |
|  |  |  |  |  | 2.96597 | 25 | 2.95740 | 60 |
|  |  |  |  |  | 2.94253 | 25 |  |  |
| 4th reflection | 2.82979 | 82.3 | 2.83556 | 91.9 | 2.75639 | 35 | 2.83264 | 85 |
| 5th reflection | 2.65877 | 98.4 | 2.66364 | 85.4 | 2.65629 | 35 | 2.64942 | 70 |
| 6th reflection | 2.56442 | 89.8 | 2.56837 | 91.9 | 2.56160 | 25 | 2.57125 | 35 |
|  |  |  |  |  |  |  | 2.56160 | 35 |
|  |  |  |  |  |  |  | 2.54726 | 70 |
| 7th reflection | 2.45204 | 45.8 | 2.45362 | 46.6 | 2.47045 | 15 | 2.43810 | 35 |
| 8th reflection | 2.37895 | 61.0 | 2.38152 | 61.5 | 2.38001 | 20 | 2.37863 | 50 |
|  |  |  |  |  |  |  | 2.37037 | 50 |
| 9th reflection | 2.26093 | 36.0 | 2.27073 | 41.8 | 2.29468 | 10 | 2.25551 | 30 |
| 10th reflection | 2.15817 | 36.2 | 2.16113 | 45.6 | 2.08980 | 20 | 2.15806 | 35 |
|  |  |  |  |  |  |  | 2.15239 | 35 |
|  |  |  |  |  |  |  | 2.04595 | 18 |
| 11th reflection | 1.69207 | 56.8 | 1.69266 | 62.0 | 1.70880 | 10 | 1.68283 | 40 |
| 12th reflection | 1.65163 | 45.5 | 1.65439 | 49.7 | 1.66911 | 10 | 1.65295 | 18 |
|  |  |  |  |  |  |  | 1.64696 | 18 |
|  |  |  |  |  |  |  | 1.64168 | 18 |
|  |  |  |  |  |  |  | 1.56875 | 14 |
| 13th reflection | 1.49000 | 100.0 | 1.49163 | 100.0 | 1.48298 | 20 | 1.48783 | 30 |
|  |  |  |  |  | 1.47074 | 15 | 1.47923 | 55 |

Measured on a D-5000 powder diffractometer from AXS-GmbH; measurement in reflection in Bragg-Brentano geometry; d (A) = lattice plane separation; I (rel) = relative intensity; data on $K_2Fe_{22}O_{34}$ from: TJBCAD, volume 72, page 49, (1973) primary reference: Dyson. D., Johnson; data on $K_2Fe_{10}O_{16}$ from ACSBA7, volume 66, page 1250, (1987) primary reference: Nariki. S., Ito. S., Yoneda. N.

Performance Tests

The catalysts are tested in a test set-up which mirrors the isothermal process operated in industry. To this end, 200 ml of solid extruded catalyst are charged into a reaction tube having an internal diameter of 30 mm. Initially, 183 ml/h of water and 168 ml/h of ethylbenzene are passed in vapor form over the catalyst for 10 days. The catalyst temperature is set at 600° C. After 10 days, the conversion (C), selectivity (S) and composition of the reaction mixture are determined by analyzing the reaction products (liquid and offgas).

Key to the Tables

At the same temperature, novel catalysts 1–8 give much higher conversions than the comparative catalysts C1 and C3. The use of these catalysts instead of the comparative catalysts therefore has the advantage that energy costs can be saved (reactor, distillative work-up). Although comparative catalyst C2 achieves comparable conversions as the novel catalysts at the same temperature, the cut hardness and thus also the mechanical stability is, however, too low to enable it to be used on an industrial scale. By contrast, catalyst C4 has disadvantages compared with the novel catalysts both in activity (lower conversions at the same temperature) and in selectivity.

TABLE 4

Properties and performance of the novel catalysts

| Example | 1 | 2 | 3 | 4 | 5 | 6 | 7 | 8 | 9 |
|---|---|---|---|---|---|---|---|---|---|
| Cut hardness [N] | 46 | 40 | 52 | 51 | 70 | 55 | 40 | 38 | 75 |
| BET surface area [m2/g] | 2.0 | 2.4 | 2.4 | 3.5 | 2.6 | 2.7 | 2.3 | 3.9 | 2.6 |
| Pore volume [ml/g] | 0.24 | 0.26 | 0.26 | 0.25 | 0.25 | 0.24 | 0.25 | 0.28 | 0.23 |
| Mean pore diameter [μm] | 0.46 | 0.45 | 0.47 | 0.46 | 0.43 | 0.45 | 0.42 | 0.32 | 0.38 |
| $U_{600°\,C.}$ | 50.6 | 50.8 | 50.8 | 49.3 | 47.3 | 50.3 | 48.6 | 52.3 | 50.8 |
| $S_{600°\,C.}$ | 95.4 | 96.0 | 96.4 | 96.5 | 96.6 | 96.5 | 97.0 | 96.2 | 96.4 |

TABLE 5

Properties and performance of the comparative catalysts

| Comparison | C1 | C2 | C3 | C4 |
|---|---|---|---|---|
| Cut hardness [N] | 35 | 17 | 60 | 68 |
| BET surface area [m$^2$/g] | 3.2 | 6.7 | 2.6 | 2.0 |
| Pore volume [ml/g] | 0.25 | 0.32 | 0.23 | 0.22 |
| Mean pore diameter [μm] | 0.24 | 0.21 | 0.20 | 0.38 |
| $C_{600°\,C.}$ | 44.1 | 49.3 | 46.2 | 47.2 |
| $S_{600°\,C.}$ | 96.8 | 96.2 | 96.7 | 95.0 |

The pore volumes were determined in accordance with DIN standard 66133.

The contact angle of the mercury during the determination of the mean pore diameter was 140° (DIN 66133).

In order to determine the cut hardness, an increasing load on the extrudate was exerted using a 0.3 mm blade until the extrudate was cut (instrument from Zwick (Ulm)). The mean of 25 extrudates was formed.

We claim:

1. A catalyst comprising iron oxide, potassium oxide, a magnesium compound, a calcium compound and a cerium compound, wherein the catalyst has one or more Fe/K phases $K_2O.Fe_2O_3$ in a ratio of $K_2O$ to $Fe_2O_3$ of 1:n, where n is a natural number from 1 to 11, has a mean pore diameter of greater than 0.35 μm and comprises 50–90% by weight of iron, calculated as $Fe_2O_3$,
1–40% by weight of potassium, calculated as $K_2O$,
5–20% by weight of cerium, calculated as $Ce_2O_3$,
0.1–10% by weight of magnesium, calculated as MgO and
1–10% by weight of calcium, calculated as CaO wherein the catalyst is produced by preparing a catalyst molding from $\alpha\text{-}Fe_2O_3$ having a mean particle dimension of greater than 0.3 μm, a potassium compound, a magnesium compound, a cerium compound and the obtained molding is calcined at temperatures above 750° C.

2. A catalyst as claimed in claim 1, wherein the catalyst has been calcined at a temperature in the range from 800 to 900° C.

3. A catalyst as claimed in claim 1, wherein the catalyst has been prepared using at least 50% by weight of $\alpha\text{-}Fe_2O_3$, based on the iron compounds employed.

4. A catalyst as claimed in claim 3, wherein the catalyst has been prepared using an $\alpha\text{-}Fe_2O_3$ having at least 50% a particle dimension of greater than 0.3 μm, based on the iron compounds employed.

5. A catalyst as claimed in claim 3, wherein the catalyst has been prepared using a mixture of 60–90% by weight of $\alpha\text{-}Fe_2O_3$ and 10–40% by weight of $\alpha\text{-}FeOOH$ as iron compound.

6. A process for the dehydrogenation of ethylbenzene to styrene, wherein the dehydrogenation is carried out in the presence of a catalyst as claimed in claim 1.

7. A process for the preparation of a catalyst comprising iron oxide, potassium oxide, a magnesium compound, a calcium compound and a cerium compound, wherein the catalyst has one or more Fe/K phases $K_2O.Fe_2O_3$ in a ratio of $K_2O$ to $Fe_2O_3$ of 1:n, where n is a natural number from 1 to 11, has a mean pore diameter of greater than 0.35 μm and comprises 50–90% by weight of iron, calculated as $Fe_2O_3$,
1–40% by weight of potassium, calculated as $K_2O$,
5–20% by weight of cerium, calculated as $Ce_2O_3$,
0.1–10% by weight of magnesium, calculated as MgO and
1–10% by weight of calcium, calculated as CaO, wherein a catalyst molding is prepared from $\alpha\text{-}Fe_2O_3$ having a mean particle dimension of greater than 0.3 μm, a potassium compound, a magnesium compound, a cerium compound and is calcined at temperatures above 750° C.

* * * * *